United States Patent [19]

Miyazaki et al.

[11] 4,409,395

[45] Oct. 11, 1983

[54] PROCESS FOR THE PRODUCTION OF GLYCOLLIC ACID ESTERS

[75] Inventors: Haruhiko Miyazaki; Koichi Hirai; Taizo Uda; Yasuo Nakamura, all of Ube; Harumi Ikezawa, Onoda; Takanori Tsuchie, Ube, all of Japan

[73] Assignee: UBE Industries, Ltd., Yanaguchi, Japan

[21] Appl. No.: 340,033

[22] Filed: Jan. 18, 1982

[30] Foreign Application Priority Data

Jan. 26, 1981 [JP] Japan ................................. 56-9064

[51] Int. Cl.³ .............................................. C07C 69/66
[52] U.S. Cl. ..................................... 560/179; 562/579
[58] Field of Search ......................... 560/179; 562/579

[56] References Cited

U.S. PATENT DOCUMENTS

| | | | |
|---|---|---|---|
| 1,962,140 | 6/1934 | Dreyfus | 562/579 |
| 1,999,403 | 4/1935 | Dreyfus | 562/579 |
| 2,091,800 | 8/1937 | Adkins et al. | 568/864 |
| 2,094,611 | 10/1937 | Lazier et al. | 560/193 |
| 2,305,104 | 12/1942 | Pardee, Jr. | 560/193 |
| 3,374,184 | 3/1968 | McEvoy et al. | 252/467 |
| 4,087,470 | 5/1978 | Suzuki | 568/864 |
| 4,112,245 | 9/1978 | Zehner et al. | 568/864 |
| 4,138,587 | 2/1979 | Yamasaki et al. | 560/204 |
| 4,229,589 | 10/1980 | Nishimura et al. | 560/193 |
| 4,229,591 | 10/1980 | Nishimura et al. | 560/193 |

FOREIGN PATENT DOCUMENTS 12468 of 1912 United Kingdom ............... 562/579

*Primary Examiner*—Paul J. Killos
*Attorney, Agent, or Firm*—Sherman & Shalloway

[57] ABSTRACT

In a process for producing a glycollic acid ester by the vapor phase catalytic hydrogenation of an oxalic acid diester in the presence of a catalyst and hydrogen gas, the improvement wherein the oxalic acid diester in the vaporous state is contacted with hydrogen gas in the presence of a catalyst composed of Ag or Pd supported on a solid carrier at a temperature of from about 120° C. to about 300° C.

10 Claims, No Drawings

PROCESS FOR THE PRODUCTION OF GLYCOLLIC ACID ESTERS

This invention relates to an improved process for the production of a glycollic acid ester by the vapor (or gaseous) phase catalytic hydrogenation of an oxalic acid diester in the presence of a catalyst and hydrogen gas. According to this process, the troubles associated with the treatment of conventional Cu/Cr type catalysts after use, especially the toxic hazard of chromium, can be obviated, and glycollic acid esters can be produced with industrial advantage from oxalic acid diesters at a high selectivity.

More specifically, this invention pertains, in a process for producing a glycollic acid ester by the vapor phase catalytic hydrogenation of an oxalic acid diester in the presence of a catalyst and hydrogen gas, to the improvement wherein the oxalic acid diester in the vaporous state is contacted with hydrogen gas in the presence of a catalyst composed of Ag or Pd supported on a solid carrier at a temperature of from about 120° to about 300° C.

A process for the production of a glycollic acid ester by the vapor phase catalytic hydrogenation of an oxalic acid diester in the presence of a catalyst and hydrogen gas has been known.

For example, such a process is suggested in German Pat. No. 459,603. According to this process, an oxalic acid diester is catalytically hydrogenated in the vapor phase in the presence of a Cu/Cr type catalyst derived from cupric carbonate and chromic acid to give a glycollic acid ester. The Cu/Cr type catalyst has generally been known as a hydrogenation catalyst for converting an ester into the corresponding alcohol by hydrogenation. This type of catalyst has excellent catalytic performance, but since it causes troubles in industrial operations, its practical value is extremely reduced. Specifically, chromium is an essential ingredient of catalysts of the above type, but it is extremely difficult to recover chromium completely from spent catalysts with good efficiency. As is well known, chromium even in trace amounts show strong toxicity to humans, and the discarding of the spent catalysts containing chromium causes serious environmental pollution.

On the other hand, various general hydrogenation catalysts other than those of the Cu/Cr type are known. Examples include metal catalysts such as Raney nickel, nickel, cobalt, copper, iron, platinum and palladium, and the oxides and sulfides of these metals. It is well known however that these general hydrogenation catalysts do not always show practical utility in all catalytic hydrogenation reactions, and unless a catalyst is selected which conforms to many different factors such as the mode and mechanism of a given reaction, the reaction conditions, etc., the desired reaction cannot be carried out with good efficiency, and moreover that there is no established guideline for the selection of such a catalyst.

Hydrogenation of an oxalic acid diester gives a glycollic acid ester, and ethylene glycol and ethanol are also formed. When the reaction product contains ethylene glycol or ethanol, it is possible to separate the glycollate from these secondary products. For this purpose, however, one additional step should be attached to the process, and this is by no means desirable. For example, British Pat. No. 2,031,883 (corresponding to Japanese Laid-Open Patent Publication No. 40685/1980) discloses a process which comprises catalytically hydrogenating an oxalic acid diester in the presence of a catalyst selected from ruthenium, nickel and Raney nickel. According to this process, either ethylene glycol or a glycollic acid ester is obtained in a larger amount by varying the reaction conditions. It is desirable however to increase the selectivity to the glycollate further and to omit the additional separating step mentioned above.

The present inventors have worked extensively in order to provide a catalyst which is free from the troubles of the Cu/Cr type catalyst in the production of a glycollic acid ester by the vapor phase catalytic hydrogenation reaction of an oxalic acid diester, and which can achieve an increased selectivity to the glycollate. It has consequently been found that a catalyst composed of Ag or Pd supported on a solid carrier, which has not been suggested previously for use in the aforesaid specified reaction, has the ability to produce a glycollic acid ester from an oxalic acid diester at an increased selectivity while advantageously avoiding the troubles associated with the treatment of the spent Cu/Cr type catalyst.

It is an object of this invention therefore to provide an improved process for producing a glycollic acid ester by the vapor phase catalytic hydrogenation of an oxalic acid diester.

The above and other objects and advantages of this invention will become more apparent from the following description.

According to the process of this invention, an oxalic acid diester is hydrogenated in the vapor phase in the presence of a catalyst composed of Ag or Pd supported on a solid carrier at a temperature of about 120° C. to about 300° C.

The catalyst used in this invention can be prepared, for example, by adding a suitable solid carrier to an aqueous solution of a water-soluble silver compound or a water-soluble palladium compound, stirring the mixture thoroughly, gradually adding a suitable alkalizing agent to the resulting suspension to deposit a precipitate containing silver or palladium on the solid carrier, collecting the solid carrier having the Ag- or Pd- containing precipitate deposited thereon, washing and drying the solid carrier, and then subjecting it to a reducing treatment. Alternatively, the addition of the alkalizing agent in the above procedure may be omitted, and the resulting suspension may be directly evaporated to dryness and subjected to a reducing treatment.

Silver nitrate, silver acetate and silver complex compounds may be cited as examples of the water-soluble silver compound. Examples of the water-soluble palladium compound include the nitrate, acetate, chloride and complex compounds of palladium. The solid carrier may, for example, include $SiO_2$, $Al_2O$, $TiO_2$, $ZnO$, $La_2O_3$, diatomaceous earth, activated carbon, etc. Examples of the alkalizing agent used in the catalyst preparation are sodium hydroxide, sodium carbonate, potassium hydroxide, aqueous ammonia, etc.

The suspension can be formed generally at room temperature, but a temperature of about 20° C. to about 30° C. may also be used. The time required for stirring the mixture for the formation of the suspension may, for example, be about 0.1 hour to about 2 hours. The concentration of the aqueous solution of the water-soluble silver or palladium compound may be selected properly. It is, for example, about 0.01 to about 30% by weight. In adding the alkalizing agent to the suspension formed as above, the alkalizing agent is preferably used in the form of an aqueous solution and added little by little. The concentration of the aqueous solution of the alkalizing agent may also be selected properly, and it is, for example, about 0.1 to about 20% by weight. The addition of the alkalizing agent can also be effected at room temperature, and cooling or heating is not particularly required. If desired, however, it may be effected at a temperature of about 20° to about 80° C. After the addition of the aqueous solution of the alkalizing agent, a period of aging, for example about 20 minutes to about 2 hours may be provided, and this is preferred. The resulting solid carrier having the Ag- or Pd-containing precipitate deposited thereon is then collected by filtration or the like, washed with water, dried in the air at a temperature of, for example, about 100° to about 150° C. and then subjected to a reducing treatment to form the catalyst used in this invention.

The reducing treatment can be carried out either in the gaseous or liquid phase. The gaseous-phase reduction can be carried out in an atmosphere of hydrogen at a temperature of, for example, about 150° C. to about 400° C. The time required for the gaseous phase reduction can be properly selected, and is, for example, from about 30 minutes to about 10 hours. The liquid-phase reduction can be carried out by using such a reducing agent as hydrazine. For example, the dried product obtained as above is put in a 1–15 wt. % aqueous solution of hydrazine, and subjected to a reducing treatment at room temperature for several to 24 hours. After the reducing treatment, the product is filtered and washed with water. The resulting solid is dried in vacuum at room temperature and again dried in vacuum at 150° to 200° C.

The amount of Ag or Pd supported on the resulting catalyst is preferably about 0.1 to about 20% by weight based on the weight of the solid carrier.

In the process of this invention, the oxalic acid diester in the vaporous state is contacted with hydrogen gas at a temperature of about 120° C. to about 300° C. The reaction temperature is preferably selected depending upon the metallic component of the catalyst, too. For example, when a catalyst composed of Ag supported on a solid carrier is used, temperatures of about 200° C. to about 240° C. are preferred, and when the metallic component is Pd, temperatures of about 130° C. to about 170° C. are preferred.

The reaction pressure can be properly selected. For example, the hydrogen pressure is from about 1 to about 20 atmospheres. The time of contact between the oxalic acid diester and the hydrogen gas and the catalyst may be properly selected. A preferred contact time is, for example, about 0.01 to about 20 seconds, more preferably about 0.2 to 8 seconds. The mole ratio of hydrogen to the oxalic acid diester in the reaction zone may be varied over a wide range. For example, it is from about 2 to about 600, preferably from about 20 to about 200.

Di($C_1$–$C_8$)alkyl esters of oxalic acid are preferred examples of the oxalic acid diester used as a starting material. Specific examples include dimethyl oxalate, diethyl oxalate, dibutyl oxalate and diamyl oxalate.

The hydrogenation catalyst used in the process of this invention does not contain chromium which poses a problem in practical application. According to the process of this invention, the desired glycollic acid ester can be obtained at a high selectivity by the catalytic hydrogenation of the oxalic acid diester. The present invention, therefore, is very desirable for practical application.

The following Examples illustrate the present invention more specifically.

EXAMPLES 1 TO 4

Five grams of silver nitrate ($AgNO_3$) was dissolved in 20 ml of water, and 145 g of 33% colloidal silica was added. The mixture was stirred at room temperature for about 1 hour. An aqueous solution of sodium hydroxide (prepared by dissolving 1.24 g of sodium hydroxide in 100 ml of water) was gradually added to the silica suspension at room temperature. After the addition, the mixture was aged for 1 hour. The precipitate was then collected by filtration. The solid (composed substantially of $AgOH$-$SiO_2$) was washed with water twice, and dried overnight at 140° C.

The resulting catalyst was treated with hydrazine before using in hydrogenation. Specifically, the catalyst composed of $AgOH$-$SiO_2$ (2 g) was taken, and 40 ml of a 3% aqueous solution of hydrazine was added. The mixture was left to stand overnight at room temperature to perform reduction. The solid was then collected by filtration, washed with water, and dried at room temperature under vacuum, and further at 150° to 200° C. under vacuum.

A stainless steel reaction tube (4 mm in inside diameter) was filled with 0.4 g of the catalyst (Ag/$SiO_2$=6.6% by weight) subjected to the above reducing treatment, and diethyl oxalate was hydrogenated under atmospheric pressure in the reaction tube at each of the reaction temperatures with each of the contact times indicated in Table 1. The results are also shown in Table 1. The mole ratio of hydrogen to diethyl oxalate in the reaction tube was set at 200.

TABLE 1

| Example | Reaction temperature (°C.) | Contact time (g.sec./ml) | Conversion of diethyl oxalate (%) | Selectivity to ethyl glycollate (%) | Selectivity to ethylene glycol (%) |
|---|---|---|---|---|---|
| 1 | 215 | 1.5 | 34.5 | 29.8 | 0 |
| 2 | 230 | 1.5 | 61.0 | 27.4 | 0 |
| 3 | 230 | 3.0 | 72.7 | 61.8 | 0 |
| 4 | 230 | 6.0 | 98.1 | 83.7 | 0 |

EXAMPLE 5

Palladium chloride ($PdCl_2$; 0.126 g) was dissolved in 150 ml of water acidified with hydrochloric acid. Then, 25 g of lanthanum oxide ($La_2O_3$) was suspended in the resulting aqueous solution at room temperature, and the mixture was vigorously stirred for 2 hours. The resulting suspension was evaporated to dryness at about 90° C. to form a brown solid. A stainless steel reaction tube (4 mm in inside diameter) was filled with 1.5 g of the solid, and hydrogen was passed through the reaction tube at 300° C. for 2 hours to perform reduction.

Diethyl oxalate was hydrogenated in the reaction tube in the presence of the resulting catalyst (Pd/$La_2O_3$=0.3% by weight) subjected to the above reducing treatment under atmospheric pressure at a reaction temperature of 145° C. with a contact time of 6.0 g.sec/ml. The mole ratio of hydrogen to diethyl oxalate in the reaction tube was set at 200.

Analysis of the reaction product showed a diethyl oxalate conversion of 51.7%, and a selectivity to ethyl glycollate of 71.2%.

EXAMPLE 6

Palladium-silica (Pd-SiO$_2$) catalyst (Pd/SiO$_2$=2% by weight, a product of Nippon Engelhaldt Co., Ltd.) was filled in a stainless steel reaction tube (4 mm in inside diameter), and the reaction temperature was maintained at 145° C. Otherwise, diethyl oxalate was catalytically hydrogenated in the same way as in Example 5.

Analysis of the reaction product showed a diethyl oxalate conversion of 55.5% and a selectivity to ethyl glycollate of 73.9%.

What we claim is:

1. In a process for producing a glycollic acid ester by the vapor phase catalytic hydrogenation of an oxalic acid diester in the presence of a catalyst and hydrogen gas, the improvement wherein the oxalic acid diester in the vaporous state is contacted with hydrogen gas in the presence of a catalyst composed of Ag supported on a solid carrier at a temperature of from about 120° C. to about 300° C.

2. The process of claim 1 wherein the contacting is carried out at a hydrogen gas pressure of about 1 to about 20 atmospheres.

3. The process of claim 1 wherein the amount of Ag supported is about 0.1 to about 20% by weight based on the weight of the solid carrier.

4. The process of claim 1 wherein the solid carrier is selected from the group consisting of SiO$_2$, Al$_2$O$_3$, TiO$_2$, ZnO, La$_2$O$_3$, diatomaceous earth and activated carbon.

5. The process of claim 1 wherein the contacting is carried out while maintaining the mole ratio of hydrogen to the oxalic acid diester at about 2 to about 600.

6. The process of claim 1 wherein the oxalic acid diester is a di(C$_1$-C$_8$)alkyl ester of oxalic acid.

7. The process of claim 6 wherein the oxalic acid diester is dimethyl oxalate, diethyl oxalate, dibutyl oxalate or diamyl oxalate.

8. The process of claim 1 wherein the temperature is from about 200° to about 240° C.

9. The process of claim 1 wherein the oxalic acid diester in the vaporous state is contacted with hydrogen gas at a mole ratio of hydrogen to the diester of about 200 in the presence of a catalyst composed of about 6.6% by weight of silver supported on SiO$_2$ as a solid carrier at a temperature of about 230° C. for a contact time of at least about 1.5 g.sec/ml.

10. The process of claim 9 wherein the contact time is from about 3.0 to about 6.0 g.sec/ml.

* * * * *